(12) United States Patent
Lahav et al.

(10) Patent No.: US 8,327,798 B2
(45) Date of Patent: Dec. 11, 2012

(54) METHODS AND COMPOSITIONS FOR INCREASING THE HATCHABILITY OF HATCHERY EGGS

(75) Inventors: Jacob Lahav, Katzerin (IL); Emil Polyansky, Carmiel (IL); Shaul Naschitz, Kibbutz El-Rom (IL)

(73) Assignee: Natratec International Ltd., Katzerin (IL)

( * ) Notice: Subject to any disclaimer, the term of this patent is extended or adjusted under 35 U.S.C. 154(b) by 357 days.

(21) Appl. No.: 12/522,628

(22) PCT Filed: Jan. 10, 2008

(86) PCT No.: PCT/IL2008/000050
§ 371 (c)(1),
(2), (4) Date: Jan. 14, 2010

(87) PCT Pub. No.: WO2008/084485
PCT Pub. Date: Jul. 17, 2008

(65) Prior Publication Data
US 2011/0126767 A1    Jun. 2, 2011

Related U.S. Application Data

(60) Provisional application No. 60/879,527, filed on Jan. 10, 2007.

(51) Int. Cl.
*A01K 45/00* (2006.01)
(52) U.S. Cl. .......................................... 119/6.8; 119/6.6
(58) Field of Classification Search .................. 119/6.6, 119/6.8
See application file for complete search history.

(56) References Cited

U.S. PATENT DOCUMENTS

| | | | |
|---|---|---|---|
| 2,734,482 A * | 2/1956 | Seltzer ........................... | 119/6.8 |
| 2,851,006 A * | 9/1958 | Taylor et al. ................... | 119/6.8 |
| 3,088,865 A | 5/1963 | Wernicoff et al. | |
| 3,088,866 A | 5/1963 | Wernicoff et al. | |
| 3,120,834 A | 2/1964 | Goldhaft et al. | |
| 3,148,649 A | 9/1964 | Moore et al. | |
| 4,556,564 A | 12/1985 | Laurent et al. | |
| 4,610,882 A | 9/1986 | Laurent et al. | |
| 4,610,883 A | 9/1986 | Laurent et al. | |
| 4,893,585 A | 1/1990 | Laurent | |
| 4,917,045 A | 4/1990 | Wiegand et al. | |
| 4,932,359 A | 6/1990 | Sheldon et al. | |
| 5,438,954 A * | 8/1995 | Phelps et al. ................... | 119/6.8 |
| 5,817,320 A * | 10/1998 | Stone ............................ | 424/278.1 |
| 7,404,375 B2 * | 7/2008 | Rajcic-Spasojevic et al. | 119/6.8 |
| 2005/0028741 A1 | 2/2005 | Spasojevic et al. | |

FOREIGN PATENT DOCUMENTS

| | | |
|---|---|---|
| EP | 0321627 A1 | 6/1989 |
| WO | 03001921 A2 | 1/2003 |

OTHER PUBLICATIONS

International Search Report dated Apr. 7, 2008 in corresponding International Application No. PCT/IL2008/000050.
De Smit et al., Embyronic developmental plasticity of the chick: Increased CO2 during early stages of incubation changes the developmental trajectories during prenatal and postnatal growth, Comparative Biochemistry and Physiology, Part A 145, 2006, pp. 166-175, Elsevier.
Sander et al., Effect of Hydrogen Peroxide Disinfection During Incubation of Chicken Eggs on Microbial Levels and Productivity, Avian Diseases, 1999, pp. 227-233, vol. 43.
Xie et al., Edible Film Coating to Minimize Eggshell Breakage and Reduce Post-Wash Bacterial Contamination Measured by Dye Penetration in Eggs, Journal of Food Science, 2002, pp. 280-284, vol. 87, No. 1, Institute of Food Technologies.
Wong et al., Evaluation of Mechanical and Barrier Properties of Protein Coatings on Shell Eggs, Poultry Science, 1996, pp. 417-422, vol. 75.

* cited by examiner

*Primary Examiner* — David Parsley
(74) *Attorney, Agent, or Firm* — The Law Office of Michael E. Kondoudis

(57) ABSTRACT

A method of hatching of hatchery eggs that includes: (a) treating the egg shell surface with a coating composition comprising a coating agent, to form a coating on the surface of the egg's shell; and (b) incubating the egg under conditions to cause hatching to occur. The hatching yield of the hatchery eggs is improved as compared to control eggs not treated as defined in (a). Also discloses is a composition for treating of hatchery eggs prior to incubation. The composition includes a coating agent, and the composition improves the hatching yield of hatchery eggs.

12 Claims, No Drawings

METHODS AND COMPOSITIONS FOR INCREASING THE HATCHABILITY OF HATCHERY EGGS

This is a national phase application under 35 USC §371 of PCT/IL08/000,050 which was filed on Jan. 10, 2008 and published as WO/2008/08448 on Jul. 17, 2008 and also claims priority under 35 USC 119(e) from U.S. provisional application 60/879,527 filed Jan. 10, 2007.

FIELD OF INVENTION

The present invention relates to methods and compositions for treating hatchery eggs.

BACKGROUND OF INVENTION

There is an increasing demand for fowl and fowl eggs, including domesticated fowl (poultry which include chickens, turkeys, ducks and geese) and wild or endangered fowl breeds.

In case of poultry the demand is mainly directed to the increase of productivity of farms producing eggs and meat. The poultry industry has grown to a large scale manufacturing industry in which more than thousands of chickens and tens of thousands of eggs are produced daily at single poultry farms or egg laying installations. Hence it is of great industrial importance to achieve greater production of eggs and also to increase the durability of the eggs while incubating and hatching. These considerations are also of high importance in case when considering wild fowl or endangered breeds, wherein the continuation of the breed is the main goal.

The ability of a developing embryo to breath during the incubation process occurs by the diffusion of gases through the shell. During incubation, an egg must lose a certain amount of its weight, mainly by the loss of water. The rate of water loss from an egg can influence the rate of embryonic development, pre-pipping oxygen consumption rate, metabolic rate, and gas exchange.

De Smit et al. [Comparative Biochemistry and Physiology, Part A, 145 (2006) 166-175] has shown that the gaseous environment in the incubator and more specifically the carbon dioxide concentration is an important parameter that can improve embryonic development and post-hatch body weight of broilers when applied at the crucial periods during incubation. Chicks incubated under increased $CO_2$ during the first 10 days had a faster embryonic growth and hatch earlier.

Even in controlled laying and incubation conditions several problems occur, which pose a significant predicament on the productions of egg and fowl. Poor results are most commonly encountered with improper control of temperature and/or humidity. When the temperature or humidity is either too high or too low for a sufficient length of incubation time, it creates severe problems in the shell condition and hence may cause abnormal growth and development of the embryo. Additional problems are encountered when improper ventilation, egg turning and sanitation of the environment. Moreover, penetration of the hatching egg shell by microorganisms results in embryonic mortality, weak egg shells, weak chicks, high chick mortality, and poor chick growth and quality for eating, laying or breeding. Furthermore, the intense genetic selection of poultry for increased body size and growth rates has adversely affected the efficiency of poultry production by causing low average hatchability rates for the eggs for many strains of domestic poultry.

Efforts to increase the hatchability of poultry eggs have included optimizing the environmental conditions during egg incubation, injection of antibiotics into eggs to control disease and treatment of the eggs with a fumigant or other type of disinfectant to reduce the number of microorganisms on the shell surface. In addition, sanitation of the hatchery building, hatchery equipment, egg transportation equipment, etc., is critical to good hatchability and high quality hatchlings.

U.S. Pat. No. 3,148,649 discloses a method and apparatus for introducing treatment materials (medicinal and food materials) into avian hatching eggs.

U.S. Pat. No. 3,120,834 relates to a method of causing adjuvants which may be in a liquid carrier to pass into the interior of an avian egg through the intact shell thereof.

U.S. Pat. No. 4,556,564 discloses that the strength of poultry eggs can be substantially enhanced by adding a small amount of zeolite A to the diet of the laying poultry. Similarly, U.S. Pat. No. 4,610,882 and U.S. Pat. No. 4,610,883 disclose that food utilization and liveability are increased when a small amount of zeolite A is added to the diet of poultry.

Several methods of directly treating the shell of poultry eggs are known in the art.

U.S. Pat. No. 4,932,359 discloses that the preliminary treatment of eggs with hydrogen peroxide decreases their contamination with microorganisms and increases the hatchability of the eggs treated.

Sanders and Wilson, [Avian Diseases, vol. 43, is. 2, pp. 227-233, 1999] demonstrated that treatment of eggs with hydrogen peroxide brings down the hatchery's bacterial contamination, yet it had no effect on either hatchability or livability of broiler stock. It did not affect their weight up to 42-day age. At the same time the loss of moisture was noted from eggs during their hatching, which could confirm a higher intensity of the metabolic processes in the eggs.

Xie et al., [*Journal of Food Science* 2002, 67:280-284] showed that coating of egg shells with edible materials such as soy protein isolate, whey protein isolate, carboxymethyl cellulose, and wheat gluten increased the mechanical properties of the treated egg shell. The study suggested that such coatings can enhance the mechanical properties of shell eggs (improve puncture strength), minimize egg microbial contamination, and may help reduce economical loss from breakage. Such improved properties of shells were also shown by Wong et al. [*Poultry Science* 1996 75:417-422], wherein shell coating was performed with mineral oils, egg albumin, soy protein isolate, wheat galoten, and corn zein.

EP0321 627 discloses a method of increasing the quality of a poultry chick wherein a small amount of zeolite is added directly to the poultry egg prior to hatching of the poultry chick. U.S. Pat. No. 4,893,585 also discloses a method of improving the hatching parameters of poultry eggs which comprises incubating the egg in specified conditions thereafter placing the incubated egg in a water suspension of zeolite.

U.S. Pat. No. 4,917,045 discloses a method for stimulating the growth of bone tissue in poultry, said method comprising treating a fertile bird egg prior to the hatching of a chick therefrom with an effective amount of a physiologically acceptable organic silicon compound.

US patent application 2005/0028741 relates to a method comprising: contacting eggs with a solution comprising a halide, thereafter incubating the eggs under conditions to promote hatch of the eggs.

WO 03/001921 discloses compositions for coating fruits, vegetables, fowl eggs, especially for organic grown produce, for protection and extension of shelf life of the fruits, vegetables, and fowl eggs.

Thus there is a widely recognized need and it will be highly advantageous to have a new method and composition for improving the hatching of hatchery eggs, which is inert, does not cause adverse effect, simplified in use, and yet which is capable of improving the hatching of hatchery eggs.

SUMMARY OF THE INVENTION

The invention relates to a method for hatching of hatchery eggs comprising:
(a) treating the egg shell surface with a coating composition comprising a coating agent, to form a coating on the surface of the egg's shell; and
(b) incubating the egg under conditions to cause hatching to occur; wherein the yield of hatching of said hatchery eggs is improved as compared to control eggs not treated as defined in (a).

The invention additionally relates to a composition for treating of hatchery eggs prior to incubation, wherein said composition comprising a coating agent, and wherein said composition improves the hatching yield of said hatchery eggs.

DETAILED DESCRIPTION OF THE INVENTION

The present invention is based on the findings that it is possible to increase the hatching yield of hatchery eggs using a coating composition comprising a coating agent, to form a coating on the surface of the egg's shell. Surprisingly it was found that treating hatchery eggs with a coating composition to form a coating on the egg's shell increases significantly the hatching yield of the hatching eggs as compared to control eggs treated under the same conditions as the hatching eggs but not contacted (treated) with the coating composition.

Thus, the invention relates to a method for hatching of hatchery eggs comprising:
(a) treating the egg shell surface with a coating composition comprising a coating agent, to form a coating on the surface of the egg's shell; and
(b) incubating the egg under conditions to cause hatching to occur; wherein the yield of hatching of said hatchery eggs is improved as compared to control eggs not treated as defined in (a).

As used herein the term "hatchery eggs" refers: especially but not limited to poultry egg, including for example chickens, turkeys, goose, ostrich, ducks, quails. Preferably the poultry egg are chickens or turkeys.

As used herein the term "coating agent" refers to a substance or mixture of substances from artificial or natural source that when applied onto the surface of the egg's shell adheres to the egg's shell surface and forms a continuous or non-continuous coating thereon.

The coating agent is preferably a material that is capable by itself of forming a coating on the surface of the egg's shell, which may be a continuous or non-continuous coating.

The coating formed of the eggs shell may be a solid, semi-solid or a liquid coating. Preferably, the coating formed on the egg's shell surface using the coating agent is a solid or semi-solid coating.

The coating may be a "continuous coating" coating a substantial portion of the egg's shell surface such that a continuous network (e.g. continuous film) on the egg's shell surface is formed. Examples of coating agents capable of forming a continuous coating are water soluble coating agents such as water soluble polymers, polysaccharides, water soluble proteins. Such water soluble coating agents are dissolved in an aqueous-based vehicle. The coating may also be a "non-continuous coating" yielding coating spots or patches (to be referred collectively as coating patches) of the coating agent on a substantial portion of the egg's shell surface. It is appreciated that part of the coating patches may be connected to each other in certain areas. Alternatively, the coating patches may be unconnected forming individual patches on the surface of the egg's shell. Examples of compositions which may yield coating patches as described above are dispersions of waxes in the composition vehicle (preferably an aqueous-based vehicle).

It is appreciated that due to the inhomogeneous surface structure of the shell surface due to the porosity of the shell surface, the coating formed thereon may have—a rough texture.

The coating formed on the egg's surface is preferably a breathing coating (or film) having a suitable porosity such that gas exchange through the egg's shell is enabled (i.e the coating has good gas permeability).

It is preferable that the coating agent does not penetrate through the shell.

In a preferred embodiment, the coating formed is characterized in that it is preferably not substantially absorbed through the egg's shell to the interior of the egg.

The improvement in hatching yield may be compared to control eggs treated in an identical manner (i.e. stored, incubated, etc. under the same condition) as the hatching eggs but not treated with a coating composition as defined in (a).

The improvement in hatch yield may be determined by comparing the hatching yield of eggs incubated following treatment of the egg shell surface with a coating composition as defined herein to eggs similarly handled and incubated but not treated in this manner (referred to as control eggs). An improvement in hatch yield (% improvement over hatching yield of non-treated eggs) may be an improvement of at least about 0.3%, 1%, 1.5%, 2%, 3%, 5%, 7%, 8%, 9%, 10%, 11%, 13%, 15% and at times even of at least about 20%. The improvement of hatching yield need to be compared with eggs that were subjected to the same handling (e.g. eggs stored for a similar time period after being laid) prior to incubation as those treated in accordance with the invention. The improvement in the hatch yield may, for example, be calculated as described in the examples under Testing Parameters, referring to the parameter difference from control (%).

The control eggs are hatching eggs of the same flock and species as the hatching eggs treated with the coating composition, which were laid at the same period of time as the hatching eggs treated with the coating composition, and treated under the same conditions (incubating, where applicable storing, etc.) as the hatching eggs treated with the coating composition.

According to a preferred embodiment inorganic materials are excluded from the coating agent. According to this preferred embodiment the coating agent does not include inorganic materials.

According to a preferred embodiment of the present invention the coating agent is an organic material (i.e. composed of an organic compound). In case of polymers, according to this preferred embodiment a coating agent which is an organic material means that the polymeric backbone in composed of an organic material.

Additionally according to a preferred embodiment of the present invention the coating agent is selected from polymers, polysaccharides, lipids, proteins, natural resins, hydrocarbons, synthetic and natural latexes, and mixtures thereof. More preferably the coating agent is a lipid.

Further according to a preferred embodiment of the present invention the polymer is a water soluble polymer.

Still further according to a preferred embodiment of the present invention the water soluble polymer is selected from polyvinyl alcohol, polyoxyethylene, polyethyleneglycol, polyacrylamide, polyvinyilpyrrolidone, polymethylvinylpyridine, and mixtures thereof. The water soluble polymer may also be a copolymer of any of the above.

Moreover according to a preferred embodiment of the present invention—the polymer is a natural modified polymer.

Preferably the natural modified polymer is selected from carboxymethylcellulose, ethylcellulose, modified starches, and mixtures thereof.

Additionally according to a preferred embodiment of the present invention the polysaccharide is selected from pectin, tree gums, guar gum, agar, xanthane gum, alginate, and mixtures thereof.

The tree gum may be gum Arabic from acacia tree.

Further according to a preferred embodiment of the present invention the lipid is selected from vegetable oils, natural waxes, and mixtures thereof. Most preferably the lipids are natural waxes.

Still further according to a preferred embodiment of the present invention the vegetable oil is selected from olive oil, rapeseed oil, corn oil, soybean oil, lecithin, palm oil, coconut oil, sunflower oil, cotton seed oil, Jojoba oil, and mixtures thereof.

Moreover according to a preferred embodiment of the present invention the natural waxes are selected from Carnauba wax, Candalilla wax, berrywax, lanolin, beeswax, montan wax, and mixtures thereof. Most preferably the natural wax is beeswax. Montan wax is also known as lignite wax.

Additionally according to a preferred embodiment of the present invention the protein is selected from albumin, casein, gelatin, gluteine, and mixtures thereof. The albumin may be egg albumin.

Further according to a preferred embodiment of the present invention the natural resin is selected from Olibanum, Myrrha, Shellac, Rosin, and mixtures thereof.

Still further according to a preferred embodiment of the present invention the hydrocarbon is selected from hard paraffins, mineral oils, vaseline, ceresin, ozocerite, and mixtures thereof.

Moreover according to a preferred embodiment of the present invention the latex (natural and synthetic latex) is selected from butadiene-styrene latex, carboxylate latex, polystyrene latex, *Hevea brasiliensis* tree latex, *Ficus elastica* tree latex, and mixtures thereof.

Natural latexes may be for example *brasiliensis* tree latex, *Ficus elastica* tree latex, and mixtures thereof.

Synthetic latexes may be for example butadiene-styrene latex, carboxylate latex, polystyrene latex, and mixtures thereof.

butadiene-styrene latex—can be obtained from Lukoil, Russia (Bulex® L-105, L-108, L-110).

Carboxylate latex can be obtained from Voronezh branch of FGUP NIISK, Russia (e.g. Latex tradename: BN-30GK, BN-40GK, BSN-GK, BS-55GK, BS-65GK, BS-75GK, BM-65GK lattices) and may refer to a product of emulsifier-free seed emulsion copolymerization of various monomers (butadiene, styrene, acrylonitrile, methyl methacrylate).

Polystyrene latex can be obtained from Ted Pella, Inc., USA (product name: polystyrene latex sphere) and is comprised of a solid polymer microspheres composed of polysterene.

*Hevea brasiliensis* tree latex can be obtained from Raintree Nutrition, Inc., USA.

The latex can be obtained by cutting the bark of this tree which releases the latex which can then be collected, preserved, and stabilized.

*Ficus elastica* tree latex can be obtained by an aqueous extraction from ficus tree.

When a range of values is indicated in the present invention, the symbol "-" has the meaning of "to". Thus, for example "0.1-5%" means "1 to 5%", "36-39° C." means "36 to 39° C.", etc. "-" and "to" may be used interchangeably in the present invention.

Preferably the concentration of said coating agent based on the total weight of the composition is in the range 0.01 to 8% w/w, more preferably 0.01 to 5% w/w, and most preferably 0.01 to 4% w/w.

When polymers are used as coating agents preferably their concentration is in the range 0.1-5% w/w (0.1 to 5% w/w), and more preferably 0.1-3% w/w, based on the total weight of the composition.

When polysaccharides are used as coating agents preferably their concentration is in the range 0.1-5% w/w, and more preferably 0.1-3% w/w, based on the total weight of the composition.

When lipids are used as coating agents preferably their concentration is in the range 0.01-5% w/w, and more preferably 0.02-4% w/w, based on the total weight of the composition.

When proteins are used as coating agents preferably their concentration is in the range 0.1-5% w/w, and more preferably 0.1-3% w/w, based on the total weight of the composition.

When natural resins are used as coating agents preferably their concentration is in the range 0.05-3% w/w, and more preferably 0.05-1.5% w/w, based on the total weight of the composition.

When hydrocarbons are used as coating agents preferably their concentration is in the range 0.05-2% w/w, and more preferably 0.1-1% w/w, based on the total weight of the composition.

When synthetic and natural latexes are used as coating agents preferably their concentration is in the range 0.1-5% w/w, and more preferably 0.1-3% w/w, based on the total weight of the composition.

The composition may comprise a vehicle. However, for certain coating agents the composition may not necessarily comprise a vehicle. For example when waxes are used as coating agents, they may be heated until they are liquefied and then for example sprayed on the egg's shell surface to form a coating thereon. Most preferably when waxes or other coating agents are used, the composition comprises a vehicle.

Preferably the composition comprises a vehicle. Preferably the vehicle is a liquid vehicle (carrier). Most preferably the vehicle (e.g. liquid vehicle) is an aqueous-based vehicle. The vehicle may further comprise alcohol. The alcohol may be for example ethanol, butanol, isopropanol, and mixtures thereof.

The alcohol content may be up to 20% w/w based on the total weight of water and alcohol in the vehicle.

Preferably the alcohol content is above zero and up to 20% w/w, more preferably the alcohol content is in the range 3 to 12% w/w, based on the total weight of water and alcohol in the vehicle.

The composition may further comprise hygroscopic agents. The hygroscopic agents may be salts (such as ammonium nitrate, calcium nitrate, calcium chloride, zinc chloride, magnesium chloride, or mixtures thereof) or organic compounds (e.g. glycerin, ethylene glycol, diethylene glycol, or mixtures thereof), or mixtures of any of the above.

The concentration of the hygroscopic agent based on the total weight of the composition may be in the range 0.01-3% w/w and more preferably 0.2-3% w/w.

The coating agent may be water-soluble or water dispersible.

The composition may further comprise an additive such as an antimicrobial agent; an antiseptic agent; an antioxidant agent (to prevent oxidation of natural oils and other components in the composition); odors; preservatives; and mixtures thereof. Such additional components may include various natural essential oils and balms as well as synthetic products having corresponding properties (i.e. antimicrobial, antiseptic, etc. mentioned above).

The composition may further comprise a member selected from an emulsifying agent (such as tween, span), suspending agents, viscosity modifiers, alkali agent (such as sodium carbonate, sodium bicarbonate, potassium carbonate, potassium bicarbonate, sodium hydroxide, potassium hydroxide), and mixtures thereof. The alkali agent functions by neutralizing part of the free fatty acids present in the coating agent (such as natural wax, for example beeswax) thus granting emulsification properties to the wax.

Thus, the final form of the composition may be a solution where the coating agent is dissolved in the vehicle and optionally the additives are dissolved or dispersed in the vehicle. The final form of the composition may also be a dispersion where the coating agent is dispersed in the vehicle and optionally the additives are dissolved or dispersed in the vehicle. Examples of such dispersions are waxes as mentioned above dispersed in an aqueous based vehicle. It is appreciated that the term dispersions encompasses solid or semi-solid material (such as waxes) dispersed in a vehicle as well as emulsions where liquid globules are dispersed in the vehicle.

According to a preferred embodiment of the present invention the hatchery egg is a poultry egg selected from chickens, turkeys, goose, ostrich, ducks, and quails.

According to one preferred embodiment the hatchery egg is a non-organic hatchery egg, more preferably non-organic poultry egg.

According to another preferred embodiment the hatchery egg is an organic hatchery egg, more preferably organic poultry egg. Where the egg is an organic hatchery egg, the coating compositions to be used should comply with organic agricultural rules. In such a case the coating composition should be such that all its components are acceptable for use in organic produce, the principal components (coating agents) of the compositions should be of natural biological origin, and the optional components have such a high grade of purity and non-toxicity that they are approved by the U.S. Food & Drug Administration for use in "biopure" products. The natural biological coating components are preferably derived from their biological sources with minimal chemical intervention, such as by gentle extraction and pressing methods, and not by chemical synthesis, and thus the components and the end-product they form, are free of synthetic additives. Examples of compositions suitable for organic agricultural use and their method of preparation are described in WO 03/001921, incorporated herein by reference in its entirety. Examples of compositions which are suitable for organic agricultural use are described for example in experiment #2 compositions 3, 4, 5, experiment #3 compositions 2, 4, 5, experiment #5 compositions 2, 3, 4, 5, experiment #6 compositions 2, 3, 4, 5, experiment #7 composition 3, experiment #8 compositions 2, 3, experiment #10 composition 5, and experiment #11 composition 2, of the present invention.

Preferably treating of the eggs is performed by means of spraying, brushing or dipping.

Preferably the improvement in hatching yield is at least 0.3%—as compared to the control eggs.

The improvement in hatching yield may be significantly higher for example about 25% (e.g. in case of storage prior to incubation). Storage prior to incubation may cause increase in hatching yield than incubation of eggs without storage. However, in reality, storage prior to incubation is sometimes unavoidable. In such case storage can yield higher hatching yield than without storage. Even in the case of eggs without prior storage, there may be an increase in hatching yield.

The improvement in hatching yield may be for example at least 1%, at least 1.5%, at least 2% at least 5%, at least 8%, at least 10%, at least 15% at least 20% as compared to the control eggs. The improvements in hatching yield maybe as indicated above and up to about 25%. The improvements in hatching yield may be as indicated above and up to about 25%, in case of normal conditions as defined below, and storage of up to 21 days.

The improvement in hatching yield depends on the storing, and incubation conditions. Generally, as the storing and incubation conditions are inferior for example in the case of a fault (such as an electrical fault) the hatching yield may be significantly higher.

Under normal condition (i.e. without any fault in storage or incubation conditions), improvement in hatching yield (as function of the storing period) may be as follows:

Without storage (0 days of storage) the hatching yield may be in the range 0.3 to 12%, or in the range 0.3% to 10.3%.

For 7 days of storage the hatching yield may be in the range 1 to 18%, or in the range 1.5 to 16.2%.

For 14 days of storage the hatching yield may be in the range 2 to 16%, or in the range 2.4 to 15.7%.

For 21 days of storage the hatching yield may be in the range 8 to 25%, or in the range 8.8 to 22.2%.

According to a preferred embodiment of the present invention the conditions (i.e. the incubation conditions) are selected from controlling temperature, relative humidity, and any combination thereof.

Preferably the temperature is in the range 36-39° C. (36 to 39° C.), and most preferably 36 to 38° C.

Preferably the relative humidity is in the range 50 to 80%. The relative humidity may be in the range 50 to 60%.

For chickens, the temperature is preferably in the range 36 to 37.7° C., and the relative humidity is preferably in the range 53 to 60%.

For turkey, the temperature is preferably in the range 36 to 37.1° C., and the relative humidity is preferably in the range 53 to 80%.

For ducks, the temperature is preferably in the range 36 to 37.8° C., and the relative humidity is preferably in the range 53 to 80%.

For goose, the temperature is preferably in the range 36 to 38.1° C., and the relative humidity is preferably in the range 53 to 80%.

The incubation conditions which may be used are described in Nirada Leksrisompong, Effect of temperature during incubation and brooding on broiler chickens, Master of Science thesis submitted to the Graduate Faculty of North Carolina State University, 2005, incorporated herein by reference in its entirety.

Various conditions for obtaining improved hatchability are described in Management of Hatching Eggs and Broiler Performance, 1 May 2002, G. D. Butcher and Amir H. Nilipour, University of Florida, IFAS extension, 1-4, incorporated herein by reference in its entirety.

Sanitation conditions for hatching eggs and its affect on hatchability are described in Henry R. Wilson, Hatching Egg Sanitation, August, 1997, pages 1-3, University of Florida, IFAS extension, incorporated herein by reference in its entirety.

The coating composition may further comprise an additive selected from an antimicrobial agent, an antiseptic agent, an antioxidant agent, a preservative, and mixtures thereof.

Preferably treating in step (a) comprises contacting the eggs with the coating composition and allowing the vehicle to evaporate to form a coating made of the coating agent on the egg's shell.

The method may further comprise prior to step (a) storing of the eggs. The storage may be for a period of up to 21 days.

The method may further comprise after step (a) and before step (b) storing of the eggs. The storage may be for a period of up to 21 days.

In case of storage, the eggs are preferably stored at a temperature range of 10-17° C. Preferably the eggs are stored at a temperature in the range of 12-17° C. The relative humidity is preferably in the range 50-53%.

Thus, the treatment of the eggs by the coating composition may be prior to their loading into the hatchery or prior to storage.

The invention additionally relates to a composition for treating of hatchery eggs, wherein said composition comprising a coating agent, and wherein said composition improves the hatching yield of said hatchery eggs.

The invention further relates to a composition for treating of hatchery eggs prior to incubation, wherein said composition comprising a coating agent, and wherein said composition improves the hatching yield of said hatchery eggs.

Preferably the composition is for use in methods as described in the present invention.

The improvement in hatching yield may be compared to control eggs treated in an identical manner (i.e. stored, incubated, etc. under the same condition) but not treated with a coating composition. The improvement may be as described above with respect to the method.

According to a preferred embodiment of the present invention the coating agent is an organic material (i.e. composed of an organic compound). In case of polymers, according to this preferred embodiment a coating agent which is an organic material means that the polymeric backbone in composed of an organic material.

Additionally according to a preferred embodiment of the present invention the coating agent is selected from polymers, polysaccharides, lipids, proteins, natural resins, hydrocarbons, synthetic and natural latexes, and mixtures thereof. More preferably the coating agent is a lipid.

Further according to a preferred embodiment of the present invention the polymer is a water soluble polymer.

Still further according to a preferred embodiment of the present invention the water soluble polymer is selected from polyvinyl alcohol, polyoxyethylene, polyethyleneglycol, polyacrylamide, polyvinyilpyrrolidone, polymethylvinylpyridine, and mixtures thereof. The water soluble polymer may also be a copolymer of any of the above.

Moreover according to a preferred embodiment of the present invention the polymer is a natural modified polymer.

Preferably the natural modified polymer is selected from carboxymethylcellulose, ethylcellulose, modified starches, and mixtures thereof.

Additionally according to a preferred embodiment of the present invention the polysaccharide is selected from pectin, tree gums, guar gum, agar, xanthane gum, alginate, and mixtures thereof.

Further according to a preferred embodiment of the present invention the lipid is selected from vegetable oils, natural waxes, and mixtures thereof. Most preferably the lipids are natural waxes.

Still further according to a preferred embodiment of the present invention the vegetable oil is selected from olive oil, rapeseed oil, corn oil, soybean oil, lecithin, palm oil, coconut oil, sunflower oil, cotton seed oil, Jojoba oil, and mixtures thereof.

Moreover according to a preferred embodiment of the present invention the natural waxes are selected from Carnauba wax, Candalilla wax, berrywax, lanolin, beeswax, montan wax, and mixtures thereof.

Additionally according to a preferred embodiment of the present invention the protein is selected from albumin, casein, gelatin, gluteine, and mixtures thereof. The albumin may be egg albumin.

Further according to a preferred embodiment of the present invention the natural resin is selected from Olibanum, Myrrha, Shellac, Rosin, and mixtures thereof.

Still further according to a preferred embodiment of the present invention the hydrocarbon is selected from hard paraffins, mineral oils, vaseline, ceresin, ozocerite, and mixtures thereof.

Moreover according to a preferred embodiment of the present invention the latex is selected from butadiene-styrene latex, carboxylate latex, polystyrene latex, *Hevea brasiliensis* tree latex, *Ficus elastica* tree latex, and mixtures thereof.

Preferably the concentration of said coating agent based on the total weight of the composition is in the range 0.01 to 8% w/w, more preferably 0.01 to 5% w/w, and most preferably 0.01 to 4% w/w.

When polymers are used as coating agents preferably their concentration is in the range 0.1-5% w/w, and more preferably 0.1-3% w/w, based on the total weight of the composition.

When polysaccharides are used as coating agents preferably their concentration is in the range 0.1-5% w/w, and more preferably 0.1-3% w/w, based on the total weight of the composition.

When lipids are used as coating agents preferably their concentration is in the range 0.01-5% w/w, and more preferably 0.02-4% w/w, based on the total weight of the composition.

When proteins are used as coating agents preferably their concentration is in the range 0.1-5% w/w, and more preferably 0.1-3% w/w, based on the total weight of the composition.

When natural resins are used as coating agents preferably their concentration is in the range 0.05-3% w/w, and more preferably 0.05-1.5% w/w, based on the total weight of the composition.

When hydrocarbons are used as coating agents preferably their concentration is in the range 0.05-2% w/w, and more preferably 0.1-1% w/w, based on the total weight of the composition.

When synthetic and natural latexes are used as coating agents preferably their concentration is in the range 0.1-5% w/w, and more preferably 0.1-3% w/w, based on the total weight of the composition.

The composition may comprise a vehicle. However, for certain coating agents the composition may not necessarily comprise a vehicle. For example when waxes are used as coating agents, they may be heated until they are liquefied and then for example sprayed on the egg's shell surface to form a coating thereon. Most preferably when waxes or other coating agents are used, the composition comprises a vehicle.

Preferably the composition comprises a vehicle. Preferably the vehicle is a liquid vehicle (carrier). Most preferably the vehicle (e.g. liquid vehicle) is an aqueous-based vehicle. The vehicle may further comprise alcohol (such as described above with respect to the method section).

The alcohol content may be up to 20% w/w based on the total weight of water and alcohol in the vehicle.

Preferably the alcohol content is above zero and up to 20% w/w based on the total weight of water and alcohol in the vehicle, more preferably the alcohol content is in the range 3 to 12% w/w.

The composition may further comprise hygroscopic agents. The hygroscopic agents may be salts (such as ammonium nitrate, calcium nitrate, calcium chloride, zinc chloride, magnesium chloride, or mixtures thereof), or organic compounds (e.g. glycerin, ethylene glycol, diethylene glycol, or mixtures thereof), or mixtures of any of the above.

The concentration of the hygroscopic agent based on the total weight of the composition may be in the range 0.01-3% w/w and more preferably 0.2-3% w/w.

The coating agent may be water-soluble or water dispersible.

The composition may further comprise an additive such as an antimicrobial agent; an antiseptic agent; an antioxidant agent (to prevent oxidation of natural oils and other components in the composition); odors, preservatives, and mixtures thereof. Such additional components may include various natural essential oils and balms as well as synthetic products having corresponding properties (i.e. antimicrobial, antiseptic, etc. mentioned above).

Thus, the final form of the composition may be a solution where the coating agent is dissolved in the vehicle and optionally the additives are dissolved or dispersed in the vehicle. The final form of the composition may also be a dispersion where the coating agent is dispersed in the vehicle and optionally the additives are dissolved or dispersed in the vehicle. Examples of such dispersions are waxes as mentioned above dispersed in an aqueous based vehicle. It is appreciated that the term dispersions encompasses solid or semi-solid material (such as waxes) dispersed in a vehicle as well as emulsions where liquid globules are dispersed in the vehicle.

According to a preferred embodiment of the present invention the hatchery egg is a poultry egg selected from chickens, turkeys, goose, ostrich, ducks, and quails.

Preferably treating of the eggs is performed by means of spraying, brushing or dipping.

Preferably the improvement in hatching yield is at least 0.3% as compared to the control eggs. The improvement in hatching yield may be as described above in the present invention with respect to the method.

According to a preferred embodiment of the present invention the conditions (i.e. the incubation conditions) are selected from controlling temperature, relative humidity, and any combination thereof.

The temperature and humidity conditions maybe as described above in the present invention with respect to the method section.

Preferably treating of the eggs comprises contacting the eggs with the coating composition and allowing the vehicle to evaporate to form a coating made of the coating agent on the egg's shell.

The treatment of the eggs by the coating composition may be prior to their loading into the hatchery or prior to storage as described above under the method part.

The compositions components, optional additives, their concentrations, the form of the final compositions, the incubation and storing conditions, etc. may be as described above in the present invention with respect to the method of hatching.

The composition described in the invention may be used in any one of the methods described in the invention.

EXAMPLES

Preparation of Coating Formulations

The coating formulations used in the specified examples were prepared using standard and known methods in the art.

When the formulation contained water soluble coating agents, e.g., polyvinyl alcohol, carboxymethyl-cellulose, gelatin, guar gum, albumin, the solutions were obtained upon dissolving the coating agents in the desired concentration in water (or water alcoholic mixture) while stirring.

In order to achieve the water-based dispersions using hydrophobic coating agents, such as lipids, natural resins, paraffins, mineral oils, intensive mixing (up to 25,000 rpm, using an homogenizer) was preformed with water (or water alcoholic mixture) in the presence of an emulsifier agent.

For hydrophobic coating agents such as lipids and paraffins the hydrophobic coating agent was heated 10-20° C. above its melting point. The aqueous medium (e.g. water) was heated at least to the temperature to which the hydrophobic material (coating agent) was heated. The aqueous medium and the hydrophobic material were combined and homogenized. The emulsifier was added prior to homogenization to the aqueous medium or hydrophobic material, depending on its solubility (for example water soluble emulsifying agent such as tween was dissolved in the aqueous medium).

Emulsions using mineral oil were prepared by the same procedure described above for lipids and paraffins, without heating.

For dispersions based on natural resins, a salt of the resin was formed in an aqueous medium by adding an alkali agent (e.g. sodium carbonate, potassium carbonate, etc.) in room temperature and homogenization was performed to form a dispersion.

Procedures for preparation of the dispersions are also described in WO 03/001921 & EP 1399026, incorporated herein by reference in their entirety.

Eggs Type

The various formulations of the invention were tested on two egg species:
 Chicken eggs (Ross and Cobb breeds)
 Turkey eggs (Nicolas breed)

Immediately after collection of the laid eggs and before storing and hatching (incubating), the eggs were divided into two groups: control group and experimental observed group (the experimental observed group was treated with the coating composition).

Over the study period, the hatchability of over 100,000 eggs was tested. Each test group consisted of at least 256 eggs (i.e. the experimental observed group consisted of at least 256 eggs, and the control group consisted of at least 256 eggs). Each experimental observed group was compared to a respective control group. The control group was treated under identical conditions (i.e. the same storage conditions, incubation conditions, and any other handling conditions used for the experimental observed group), with the difference that the control group was not treated with the coating composition.

Treatment of the Eggs

Prior to storage, the experimental observed eggs were sprayed (or immersed or brushed) with the coating composition to form a coating thereon. In case the eggs were not stored they were treated with the coating composition and transferred directly to incubation.

Storage and Hatchery Conditions

Prior to hatching of the eggs, the eggs were stored for 0, 7, 14 or 21 days in the air ventilated room, with temperature at about 14° C. "0" days means that the eggs were not stored prior to hatching.

Hatching was performed using box type hatcher with capacity of 4,500 chicken eggs. Within the box type hatcher, the eggs were re-positioned. Eggs were subsequently transferred (on the 18$^{th}$ day for chickens and on the 24$^{th}$ day for turkeys) to a hatcher in the main hatchery area for additional 3-4 days (which is similar to the box type hatcher, but without movement of the eggs). In the box type hatcher the temperature was 37.5° C. and the relative humidity level was 50%. These conditions were sustained throughout the entire hatching time in the box type hatcher. Within the hatcher, the temperature was sustained at a level of 37.5° C. and 53% relative humidity level.

Testing Parameters

Subsequent to the hatching of the eggs the various parameters of the hatchability of the eggs were analyzed using the waste of hatching (the waste of hatching refers to the residual material (non-hatched eggs) such as unfertile eggs, cracked eggs, etc. as described below). The estimation of the hatchability level (hatching rate in %) in the observed group and the control group, was preformed taking into consideration only the "potential hatching eggs". All eggs which in normal (ideal) conditions were in feasibility to produce chicks were taken into consideration (referred here as "potential hatching eggs"). The sum of the "potential hatching eggs" was based on the number of the hatched eggs and the number of non-hatched eggs excluding the eggs which were non-hatched due to the following parameters: non-fertility, contamination, crakes in the egg's shell, invert eggs.

After completion of the study the non-hatched eggs were analyzed according to the above-mentioned parameters.

The hatch rate (%) was calculated as the percentage of the hatched eggs from the total sum of the potential hatching eggs.

The difference from control (%) was calculated as follows: $(100X/C)-100$, where X is the hatch rate of the observed group treated with the coating composition and C is the hatch rate of the control group.

During the testing process, eggs were not categorized according to their size, form and other physical characteristics.

In the compositions described below the composition components in % refer to w/w percentage based on the total weight of the composition.

Experiments 1-11 were conducted on chicken eggs. Experiment 12 was conducted on turkey eggs.

Results

Experiment No. 1

| | Days of Storage | | | | | |
|---|---|---|---|---|---|---|
| | 0 | | 7 | | 14 | |
| Compound Composition | Hatch rate (%) | Difference (% from control) | Hatch rate (%) | Difference (% from control) | Hatch rate (%) | Difference (% from control) |
| 1 Control | 87.4 | | 77.8 | | 71.8 | |
| 2 Polyvinyl alcohol 1% Water up to 100% | 95.6 | +9.4 | 86.8 | +11.6 | 82.3 | +14.6 |
| 3 Polyvinylpyrrolidone 0.5% Ethanol 8% Water up to 100% | 91.7 | +4.9 | 90.4 | +16.2 | 83.1 | +15.7 |
| 4 Copolymer of polyacrylamide and poly methylvinylpyridine (weight ratio 40/60) 0.3% Ethanol 8% Water up to 100% | 93.5 | +7.0 | 88.1 | +13.2 | 82.3 | +14.6 |
| 5 Polyethylene glycol (M.W. 1000) 1.7% Water up to 100% | 89.6 | +2.5 | 87.7 | +12.7 | 81.7 | +13.8 |

Experiment No. 2

| | Days of Storage | | | | | |
|---|---|---|---|---|---|---|
| | 0 | | 7 | | 14 | |
| Compound Composition | Hatch rate (%) | Difference (% from control) | Hatch rate (%) | Difference (% from control) | Hatch rate (%) | Difference (% from control) |
| 1 Control | 84.5 | | 81.2 | | 75 | |
| 2 Carboxymethyl cellulose 2% Butanol 2% Water up to 100% | 90.3 | +6.9 | 85.9 | +5.8 | 86.7 | +15.6 |

-continued

|   | Compound Composition | Days of Storage | | | | | |
|---|---|---|---|---|---|---|---|
|   |   | 0 | | 7 | | 14 | |
|   |   | Hatch rate (%) | Difference (% from control) | Hatch rate (%) | Difference (% from control) | Hatch rate (%) | Difference (% from control) |
| 3 | Guar gum 0.2%<br>Ethanol 20%<br>Water up to 100% | 93.2 | +10.3 | 84.8 | +4.4 | 84 | +12.0 |
| 4 | Pectin 0.3%<br>Ethanol 15%<br>Water up to 100% | 91.5 | +8.3 | 85.3 | +5.0 | 83.6 | +11.5 |
| 5 | Sodium alginate 0.5%<br>Ethanol 10%<br>Water up to 100% | 88.9 | +5.2 | 83.7 | +3.1 | 81.9 | +9.2 |

Experiment No. 3

|   | Compound Composition | Days of Storage | | | | | |
|---|---|---|---|---|---|---|---|
|   |   | 0 | | 7 | | 14 | |
|   |   | Hatch rate (%) | Difference (% from control) | Hatch rate (%) | Difference (% from control) | Hatch rate (%) | Difference (% from control) |
| 1 | Control | 85.1 |   | 78.2 |   | 74.5 |   |
| 2 | Egg Albumin 1%<br>Ethanol 12%<br>Water up to 100% | 89.5 | +5.2 | 82.7 | +5.7 | 78.6 | +5.5 |
| 3 | Sodium caseinate 3%<br>Isopropanol 10%<br>Water up to 100% | 90.3 | +6.1 | 83.4 | +6.6 | 77.9 | +4.6 |
| 4 | Gelatine 0.7%<br>Ethanol 12%<br>Water up to 100% | 92 | +8.1 | 85.4 | +9.2 | 82.7 | +11.0 |
| 5 | Soybean protein 0.5%<br>Ethanol 12%<br>Water up to 100% | 88.7 | +4.2 | 82.2 | +5.1 | 77.8 | +4.4 |

Experiment No. 4

|   | Compound Composition | Days of Storage | | | | | |
|---|---|---|---|---|---|---|---|
|   |   | 0 | | 7 | | 14 | |
|   |   | Hatch rate (%) | Difference (% from control) | Hatch rate (%) | Difference (% from control) | Hatch rate (%) | Difference (% from control) |
| 1 | Control | 89.2 |   | 82.4 |   | 78.2 |   |
| 2 | Butadiene-styrene latex 0.1%<br>Polyoxyethelene 0.3%<br>Isopropanol 5%<br>Water up to 100% | 91.6 | +2.7 | 85.4 | +3.6 | 81 | +3.6 |
| 3 | Polystyrene latex 0.2%<br>Water up to 100% | 90.8 | +1.8 | 86.7 | +5.2 | 82.2 | +5.1 |
| 4 | *Ficus elastica* tree latex 0.15%<br>Ethylcellulose 0.6%<br>Butanol 5%<br>Water up to 100% | 91.1 | +2.1 | 85.1 | +3.3 | 80.7 | +3.2 |
| 5 | *Hevea brasiliensis* tree latex 0.4%<br>Water up to 100% | 91.5 | +2.6 | 86.2 | +4.6 | 80.4 | +2.8 |

Note:
The concentration of latexes in the final composition refers to the concentration of the "dry matter" of the latex.

Experiment No. 5

| | Compound Composition | Days of Storage | | | | | | | |
|---|---|---|---|---|---|---|---|---|---|
| | | 0 | | 7 | | 14 | | 21 | |
| | | Hatch rate (%) | Difference (% from control) | Hatch rate (%) | Difference (% from control) | Hatch rate (%) | Difference (% from control) | Hatch rate (%) | Difference (% from control) |
| 1 | Control | 85.9 | | 80.3 | | 76.7 | | 67.9 | |
| 2 | Beeswax 1%<br>Ethanol 4%<br>Sodium Carbonate ~0.06%<br>(until pH level 9)<br>Water up to 100% | 90.3 | +5.1 | 87.1 | +8.5 | 80.8 | +5.3 | 76.4 | +12.5 |
| 3 | Beeswax 0.4%<br>Olive oil 0.1%<br>Ethanol 12%<br>Sodium Carbonate ~0.02%<br>(until pH level 8.5)<br>Water up to 100% | 91.5 | +6.5 | 86.3 | +7.5 | 78.7 | +2.6 | 77.4 | +14.0 |
| 4 | Beeswax 1%<br>Jojoba oil 0.5%<br>Ethanol 10%<br>Sodium Carbonate ~0.06%<br>(until pH level 9)<br>Water up to 100% | 89.6 | +4.3 | 85.8 | +6.8 | 79.5 | +3.6 | 73.9 | +8.8 |
| 5 | Berrywax 4%<br>Lecithin 1%<br>Ethanol 12%<br>Potassium hydroxide ~0.15%<br>(until pH level 8.5)<br>Water up to 100% | 92.1 | +7.2 | 86.4 | +7.6 | 82.3 | +7.3 | 75 | +10.5 |

Experiment No. 6

| | Compound Composition | Days of Storage | | | | | | | |
|---|---|---|---|---|---|---|---|---|---|
| | | 0 | | 7 | | 14 | | 21 | |
| | | Hatch rate (%) | Difference (% from control) | Hatch rate (%) | Difference (% from control) | Hatch rate (%) | Difference (% from control) | Hatch rate (%) | Difference (% from control) |
| 1 | Control | 84.2 | | 78.9 | | 73.9 | | 64.8 | |
| 2 | Candelilla wax 0.8%<br>Lecitin 0.03%<br>Ethanol 12%<br>Sodium Carbonate ~0.01%<br>(until pH 8)<br>Water up to 100% | 91.1 | +8.2 | 86.7 | +9.9 | 82.9 | +12.2 | 78.4 | +21.0 |
| 3 | Beeswax 0.2%<br>Carnauba wax 0.2%<br>Ethanol 12%<br>Sodium Carbonate ~0.01%<br>(until pH level 9)<br>Water up to 100% | 92.5 | +9.9 | 85.8 | +8.7 | 83.6 | +13.1 | 75.2 | +16.0 |
| 4 | Candelilla wax 0.3%<br>Sybean oil 0.1%<br>Lecithin 0.02%<br>Ethanol 12%<br>Water up to 100% | 90.7 | +7.7 | 87 | +10.3 | 84.7 | +14.6 | 77.3 | +19.3 |
| 5 | Sunflower oil 0.15%<br>Palm oil 0.15%<br>Lecithin 1%<br>Ethanol 10%<br>Water up to 100% | 89.2 | +5.9 | 87.4 | +10.8 | 81.8 | +10.7 | 79.2 | +22.2 |

Experiment No. 7

| | Compound Composition | Days of Storage | | | | | |
|---|---|---|---|---|---|---|---|
| | | 0 | | 7 | | 14 | |
| | | Hatch rate (%) | Difference (% from control) | Hatch rate (%) | Difference (% from control) | Hatch rate (%) | Difference (% from control) |
| 1 | Control | 87.6 | | 83.8 | | 77.8 | |
| 2 | Montan wax 1%<br>Ethanol 6%<br>Sodium Carbonate ~0.06%<br>(until pH level 9)<br>Water up to 100% | 92.7 | +5.8 | 86.1 | +3.4 | 81.9 | +5.3 |
| 3 | Lanolin 0.4%<br>Beeswax 0.4%<br>Ethanol 10%<br>Sodium Carbonate ~0.03<br>(until pH level 8)<br>Water up to 100% | 93.3 | +6.5 | 85.9 | +3.1 | 84.2 | +8.2 |
| 4 | Ceresine 0.7%<br>Cotton seed oil 0.15%<br>Lecithin 0.05%<br>Ethanol 10%<br>Water up to 100% | 90.7 | +3.5 | 85.8 | +3.0 | 82.6 | +6.2 |
| 5 | Ceresine 0.2%<br>Rape oil 0.02%<br>Lecitin 0.02%<br>Ethanol 10%<br>Water up to 100% | 89.6 | +2.3 | 86.4 | +3.7 | 83.5 | +7.3 |

Experiment No. 8

| | Compound Composition | Days of Storage | | | | | |
|---|---|---|---|---|---|---|---|
| | | 0 | | 7 | | 14 | |
| | | Hatch rate (%) | Difference (% from control) | Hatch rate (%) | Difference (% from control) | Hatch rate (%) | Difference (% from control) |
| 1 | Control | 88.9 | | 85.7 | | 82 | |
| 2 | Rosin 0.3%<br>Sodium Carbonate 0.15%<br>Water up to 100% | 89.7 | +0.9 | 87.4 | +2.0 | 84.3 | +2.8 |
| 3 | Olibanum 0.5%<br>Lecithin 0.2%<br>Ethanol 8%<br>Sodium Carbonate 0.01%<br>Water up to 100% | 91.2 | +2.6 | 89.5 | +4.4 | 84 | +2.4 |
| 4 | Shellac 0.4%<br>Sodium Carbonate 0.15%<br>Water up to 100% | 89.2 | +0.3 | 86.6 | +1.1 | 86.4 | +5.4 |
| 5 | Rosin 0.3%<br>Myrrha 0.4%<br>Shellac 0.1%<br>Sodium Carbonate 0.5%<br>Ethanol 5%<br>Water up to 100% | 91.5 | +2.9 | 90.7 | +5.8 | 85.1 | +3.8 |

Experiment No. 9

| | Compound Composition | Days of Storage | | | | | |
|---|---|---|---|---|---|---|---|
| | | 0 | | 7 | | 14 | |
| | | Hatch rate (%) | Difference (% from control) | Hatch rate (%) | Difference (% from control) | Hatch rate (%) | Difference (% from control) |
| 1 | Control | 86.4 | | 82.1 | | 78.3 | |
| 2 | Paraffin 0.2% (melting point 55-80° C.) Butanol 20% Tween 80 0.05% Water up to 100% | 88.9 | +2.9 | 85.9 | +4.6 | 84.2 | +7.5 |
| 3 | Paraffin 0.1% (melting point 55-80° C.) Ozocerite 0.2% Butanol 5% Tween 80 0.1% Water up to 100% | 87.6 | +1.4 | 86.4 | +5.2 | 85.6 | +9.3 |
| 4 | Mineral oil 0.7% Butanol 10% Tween 80 0.1% Water up to 100% | 88.2 | +2.1 | 86.5 | +5.4 | 82.7 | +5.6 |
| 5 | Vaseline 1% Tween 80 0.1% Water up to 100% | 90 | +4.2 | 87.4 | +6.4 | 83.8 | +7.0 |

Experiment No. 10

| | Compound Composition | Days of Storage | | | | | |
|---|---|---|---|---|---|---|---|
| | | 0 | | 7 | | 14 | |
| | | Hatch rate (%) | Difference (% from control) | Hatch rate (%) | Difference (% from control) | Hatch rate (%) | Difference (% from control) |
| 1 | Control | 91.6 | | 84.8 | | 80.6 | |
| 2 | Ozocerite 0.5% Mineral oil 0.2% Isopropanol 10% Tween 80 0.1% Water up to 100% | 93.2 | +1.7 | 88.3 | +4.1 | 85.1 | +5.6 |
| 3 | Paraffin 0.1% (melting point 55-80° C.) Corn oil 0.2% Lecithin 0.5% Isopropanol 15% Tween 80 0.1% Water up to 100% | 93.8 | +2.4 | 86.1 | +1.5 | 85.4 | +5.9 |
| 4 | Starch modified 1.5% Ethanol 12% Water up to 100% | 94 | +2.6 | 88.9 | +4.8 | 84.5 | +4.8 |
| 5 | Tree gum 0.5% Agar 0.1% Ethanol 15% Water up to 100% | 92.8 | +1.3 | 87.5 | +3.2 | 83.7 | +3.8 |

Experiment No. 11

| | | Days of Storage | | | | | |
|---|---|---|---|---|---|---|---|
| | | 0 | | 7 | | 14 | |
| | Compound Composition | Hatch rate (%) | Difference (% from control) | Hatch rate (%) | Difference (% from control) | Hatch rate (%) | Difference (% from control) |
| 1 | Control | 90.3 | | 83.6 | | 79 | |
| 2 | Rosin 0.2%<br>Xanthan gum 0.3%<br>Ethanol 10%<br>Sodium Carbonate 0.1%<br>Water up to 100% | 94.6 | +4.8 | 88.2 | +5.5 | 85.7 | +8.5 |
| 3 | Carboxylate latex 0.2%<br>Water up to 100% | 91.9 | +1.8 | 85.2 | +1.9 | 84.5 | +7.0 |
| 4 | Lanolin 0.6%<br>Coconut oil 0.05%<br>Lecithin 0.05%<br>Ethanol 12%<br>Water up to 100% | 93.8 | +3.9 | 87.2 | +4.3 | 83.8 | +6.1 |
| 5 | Berrywax 1.2%<br>Shellac 0.05%<br>Ethanol 5%<br>Sodium Carbonate 0.03%<br>Water up to 100% | 92.5 | +2.4 | 90.3 | +8.0 | 87.3 | +10.5 |

Note:
The concentration of latexes in the final composition refers to the concentration of the "dry matter" of the latex.

Experiment No. 12

| | | Days of Storage | | | | | |
|---|---|---|---|---|---|---|---|
| | | 0 | | 7 | | 14 | |
| | Compound Composition | Hatch rate (%) | Difference (% from control) | Hatch rate (%) | Difference (% from control) | Hatch rate (%) | Difference (% from control) |
| 1 | Control | 85.5 | | 74.7 | | 69.3 | |
| 2 | Polyvinylpyrrolidone 0.5%<br>Ethanol 8%<br>Water up to 100% | 90.2 | +5.5 | 82.6 | +10.6 | 74.1 | +6.9 |
| 3 | Carboxymethyl cellulose 2%<br>Butanol 2%<br>Water up to 100% | 89.4 | +4.6 | 82 | +9.8 | 74 | +6.8 |
| 4 | Candelilla wax 0.3%<br>Soybean oil 0.1%<br>Lecithin 0.02%<br>Ethanol 12%<br>Water up to 100% | 91.3 | +6.8 | 80.6 | +7.9 | 74.1 | +6.9 |
| 5 | Paraffin 0.1%<br>Corn oil 0.2%<br>Lecithin 0.5%<br>Isopropanol 15%<br>Tween 80 0.1%<br>Water up to 100% | 88.6 | +3.6 | 78.5 | +5.0 | 72.6 | +4.8 |

In the above experiments:

Butadiene-styrene latex used is a water-polymer emulsion of butadiene and styrene (Butlex® L-108 obtained from Lukoil, USA).

Polyoxyethelene used refers to polyethelene oxide having a molecular weight of 300,000.

Polystyrene latex used comprises solid polymer microspheres composed of polysterene (1 micrometer). The polysterene latex (product name: Polystyrene latex sphere) was obtained from Ted Pella, Inc., USA.

*Ficus elastica* tree latex refers to an aqueous extraction from ficus tree (Israel).

*Hevea brasiliensis* tree latex was obtained from Raintree Nutrition, Inc., USA.

Starch modified used is Vitex obtained from GFS Chemicals, USA (CAS #9005-84-9).

Tree gum used is gum Arabic from acacia tree (CAS #9000-01-5) obtained from Sigma-Aldrich.

Carboxylate latex used is BM-65GK (Latex trademark), a heteropolymer carboxylated lattice, obtained from Voronezh branch of FGUP NIISK, Russia. BM-65GK lattice is a product of emulsifier-free seed emulsion copolymerization of butadiene, styrene, acrylonitrile, methyl methacrylate.

The above examples demonstrate that treatment with the coating compositions of the present invention will result in an increased hatchability of hatchery eggs.

The proposed method may be successfully used not only to increase the hatchability of eggs designated for immediate hatchery but also in the cases requiring preliminary storage of eggs for the period of up to 2-3 weeks.

While this invention has been shown and described with reference to preferred embodiments thereof, it will be understood by those skilled in the art that many alternatives, modifications and variations may be made thereto without departing from the spirit and scope of the invention. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference.

What is claimed is:

1. A composition formulated for improving hatchery eggs prior to incubation, comprising an aqueous-based vehicle and a coating agent selected from the group consisting of polymers, polysaccharides, lipids, proteins, natural resins, hydrocarbons synthetic and natural latexes and mixtures thereof, the coating agent concentration being in the composition in a range of 0.01% and 8% w/w, the composition being suitable for forming a porous coating over the egg's shell surface to thereby improve the hatching yield of said hatchery eggs as compared to hatching yield of hatchery eggs without the shell surface coating.

2. A composition according to claim 1, wherein the coating agent comprises at least one water soluble polymer selected from the group consisting of polyvinyl alcohol, polyoxyethylene, polyacrylamide, polyvinyilpyrrolidone, and polymethylvinylpyridine.

3. A composition according to claim 1, wherein the coating agent comprises at least one modified natural polymer selected from the group consisting of carboxymethylcellulose, ethylcellulose, and modified starches.

4. A composition according to claim 1, wherein the coating agent comprises at least one polysaccharide selected from the group consisting of pectin, tree gums, guar gum, agar, xanthane gum and alginate.

5. A composition according to claim 1, wherein the coating agent comprises at least one protein selected from the group consisting of albumin, casein, gelatin and gluteine.

6. A composition according claim 1, wherein said aqueous-based vehicle comprises an alcohol content up to 20% w/w.

7. A composition according claim 1, wherein said coating agent is water-soluble or water dispersible.

8. A composition according to claim 1, suitable for forming a coating over the egg's shell surface in the form selected from a continuous network, coating spots or patches.

9. A composition according to claim 1, wherein said coating agent is water soluble or water dispersible.

10. A composition according to claim 1, wherein the coating agent is essentially free of inorganic material.

11. A composition formulated for improving hatchery eggs prior to incubation, comprising an aqueous-based vehicle and a water soluble or water dispersible coating agent selected from the group consisting of polymers, polysaccharides, lipids, proteins, natural resins, a hydrocarbons and mixtures thereof, the coating agent concentration being in the composition in a range of 0.01% and 8% w/w, the composition being suitable for forming a porous coating over the egg's shell surface to thereby improve the hatching yield of said hatchery eggs as compared to hatching yield of hatchery eggs without the shell surface coating.

12. A composition according to claim 11, suitable for forming, upon evaporation of said aqueous-based vehicle, a coating over the egg's shell surface in the form selected from a continuous network, coating spots or patches.

* * * * *